US012560613B2

(12) United States Patent
 Morrison

(10) Patent No.: US 12,560,613 B2
(45) Date of Patent: Feb. 24, 2026

(54) NANOSPRAY REACTIVE SPRAYER

(71) Applicant: Waters Technologies Corporation, Milford, MA (US)

(72) Inventor: Lindsay Morrison, Waltham, MA (US)

(73) Assignee: Waters Technologies Corporation, Milford, MA (US)

( * ) Notice: Subject to any disclaimer, the term of this patent is extended or adjusted under 35 U.S.C. 154(b) by 540 days.

(21) Appl. No.: 18/096,059

(22) Filed: Jan. 12, 2023

(65) Prior Publication Data

US 2023/0243844 A1     Aug. 3, 2023

Related U.S. Application Data

(60) Provisional application No. 63/305,920, filed on Feb. 2, 2022.

(51) Int. Cl.
 *G01N 33/68*     (2006.01)
 *B05B 5/03*     (2006.01)
 *B05B 5/08*     (2006.01)

(52) U.S. Cl.
 CPC ........... *G01N 33/6848* (2013.01); *B05B 5/03* (2013.01); *B05B 5/087* (2013.01)

(58) Field of Classification Search
 CPC ......... B05B 5/005; B05B 5/03; B05B 5/0533; B05B 5/087; B05B 5/1608;
 (Continued)

(56) References Cited

U.S. PATENT DOCUMENTS 7,960,711 B1 *   6/2011   Sheehan ................ H01J 49/165
                                                       250/493.1
9,362,102 B2   6/2016   Dovichi et al.
                   (Continued)

FOREIGN PATENT DOCUMENTS

WO          9858745 A1    12/1998
WO       2020243960 A1    12/2020

OTHER PUBLICATIONS

International Preliminary Report on Patentability in PCT/US2023/010647 mailed on Aug. 15, 2024.
"Michaelis-Menten Kinetics and Briggs-Haldane Kinetics" Dec. 2007, University of Washington; https://depts.washington.edu/wmatkins/kinetics/michaelis-menten.html.
Vakil, Elham and Manuel Gamero-Castano, "Investigation of the electrostatic focusing of beams of electrosprayed nanodroplets for microfrabrication applications," Dec. 2019, AIP Advances; DOI: https://doi.org/10.1063/1.5128113.
 (Continued)

*Primary Examiner* — Jennifer Wecker
(74) *Attorney, Agent, or Firm* — Schmeiser, Olsen & Watts LLP; William G. Guerin, Esq.

(57)          ABSTRACT

Described are an apparatus for generating and collecting nanospray reactive droplets and a method for analyzing a protein digestion. The apparatus includes a capillary, counter electrode, collection vessel, electrostatic lenses, and voltage control module. The capillary receives a mixture that includes a protein and an enzyme and has an outlet disposed in the aperture to dispense the mixture. The collection vessel has a concave surface to receive a nanospray plume emitted from the capillary outlet. The counter electrode and electrostatic lenses are disposed along a nanospray path defined between the capillary outlet and the collection vessel. Each electrostatic lens is formed of an electrically conductive plate having an aperture therein to pass a nanospray reactive plume. The voltage control module is in electrical communication with and is configured to independently control the voltage of the capillary, the counter electrode, the collection vessel and each of the electrostatic lenses.

14 Claims, 9 Drawing Sheets

(58) Field of Classification Search
   CPC ....... G01N 2030/8831; G01N 30/7266; G01N
                                    33/6848; H01J 49/04
   See application file for complete search history.

(56)                    References Cited

U.S. PATENT DOCUMENTS

| | | |
|---|---|---|
| 2002/0011560 A1 | 1/2002 | Sheehan et al. |
| 2006/0252047 A1 | 11/2006 | Ekstrom et al. |
| 2012/0153143 A1 | 6/2012 | Kennedy et al. |
| 2016/0086785 A1* | 3/2016 | Chiu .................... H01J 49/165 |
| | | 239/3 |
| 2020/0381235 A1 | 12/2020 | Murray et al. |

OTHER PUBLICATIONS

Iyer, et al. "Ion Manipulation in Open Air Using 3D-Printed Electrodes," 2019, Journal of American Society for Mass Spectometry, No. 30, pp. 2584-2593; DOI: 10.1007/s13361-019-02307-2.
Lee, et al. "Fabrication of a protein film by electrospray deposition method and investigation of photochemical properties by persistent spectral hole burning" Biomaterials, vol. 24, No. 12, May 1, 2003.
International Search Report and Written Opinion in PCT/US2023/010647 mailed on May 9, 2023.

\* cited by examiner

10

20

NEBULIZER
GAS

16

NANOSPRAY
PLUME
18

A: (R)VNSAAFPAPIEK(T)     D: (K)APQVYTIPPPKEQMAK(D)

B: (R)SVSELPIMHQDWLNGK(E)     E: (R)ITISK(D)

C: (R)VNSAAFPAPIEK(T)

NANOSPRAY REACTIVE SPRAYER

RELATED APPLICATION

This application is a non-provisional patent application claiming priority to U.S. Provisional Patent Application No. 63/305,920, filed Feb. 2, 20202, titled "Nanospray Reactive Sprayer," which is incorporated herein by reference in its entirety.

FIELD OF THE INVENTION

The disclosed technology relates generally to an apparatus that concentrates a nanospray reactive plume and electrodeposits the plume nanodroplets into a collection vessel. Rehydration of the electrodeposited material can be performed to prepare a sample for subsequent analysis, for example, by a liquid chromatography-mass spectrometry (LC-MS) system.

BACKGROUND

Reactions and enzymatic digests used in preparation for LC-MS analysis often require extensive reaction times. Consequently, these preparative steps can be the rate-limiting factor in generating LC-MS measurement data for particular quality attributes in bioprocessing applications and for analytical characterizations. The use of microfluidics and nanodroplets can enable reaction acceleration; however, infusion of heterogeneous mixtures can result in ion suppression and potentially lead to failed identification of low abundance, modified peptides. In addition, buffers and reagents typically used for protein digests are often non-volatile and therefore are often not ideal for direct mass spectrometry analysis.

Electrospray ionization (ESI) techniques are sometimes used to improve the reaction rate. Generally, ESI applications are based on formation of a droplet plume in which nascent droplets formed at the tip of an emitter sequentially evaporate and collect charge before undergoing repeated fission events that result in the generation of smaller, high velocity droplets. This process results in a spray plume that rapidly diverges and is difficult to directly collect. The high velocity droplets bounce off the surface of a collection device, especially for decreasing droplet sizes, further increasing the difficulty of collection.

SUMMARY

In one aspect, an apparatus for generating and collecting nanospray reactive droplets includes a capillary, counter electrode, collection vessel, a plurality of electrostatic lenses, and a voltage control module. The capillary has a capillary inlet to receive a mixture of a protein and an enzyme and a capillary outlet to dispense the mixture. The counter electrode is formed of an electrically conductive plate having an aperture therein wherein the capillary outlet is disposed in the aperture. The collection vessel is formed of an electrically conductive material and has a concave surface to receive a nanospray plume emitted from the capillary outlet. The capillary and the collection vessel are disposed on a nanospray path extending between the capillary outlet and the collection vessel. The lenses are disposed along the nanospray path. Each electrostatic lens is formed of an electrically conductive plate having an aperture therein to pass the nanospray plume. The voltage control module is in electrical communication with and configured to independently control the voltage of the capillary, the counter electrode, the collection vessel and each of the electrostatic lenses.

The collection vessel may be perforated to enable liquid comprising nanospray reactive droplets incident on the concave surface to be extracted. The concave surface may be a conical surface.

The apparatus may further include a nebulizer that is disposed proximate to the capillary output and has a mixture inlet to receive the mixture of the protein and the enzyme, a gas inlet to receive a nebulizer gas and a nebulizer outlet to provide a nebulized flow of the dispensed mixture. The nebulizer may have a pair of gas inlets wherein the gas inlets are disposed diametrically opposite to each other with respect to an axis defined between the mixture inlet and the nebulizer outlet.

The position of each of the electrostatic lenses along the nanospray path may be adjustable. The electrospray path may be oriented vertical with respect to gravity.

In another aspect, a method for analyzing a protein digestion includes providing a solution containing a protein and an enzyme and electrospraying the solution to form a nanospray plume of nanodroplets to accelerate a protein digestion. The method further includes concentrating the nanospray plume onto a surface of a collection vessel.

Providing the solution may include providing a solution containing a protein, an enzyme and one or more buffer components.

A diameter of the nanospray plume at the collection vessel may be less than a maximum diameter of the nanospray plume at an upstream position in the nanospray path.

The method may further include collecting a liquid formed by the nanospray plume incident at the surface of the collection vessel to generate a sample. Collecting the liquid may include drying the liquid on the surface of the collection vessel to generate a residue and subsequently solvating the residue to generate a resuspended sample. The method may further include performing a liquid chromatography analysis of the sample or the resuspended sample.

BRIEF DESCRIPTION OF THE DRAWINGS

The above and further advantages of this invention may be better understood by referring to the following description in conjunction with the accompanying drawings, in which like numerals indicate like structural elements and features in the various figures. For clarity, not every element may be labeled in every figure. The drawings are not necessarily to scale, emphasis instead being placed upon illustrating the principles of the invention.

DETAILED DESCRIPTION

Figure 1:
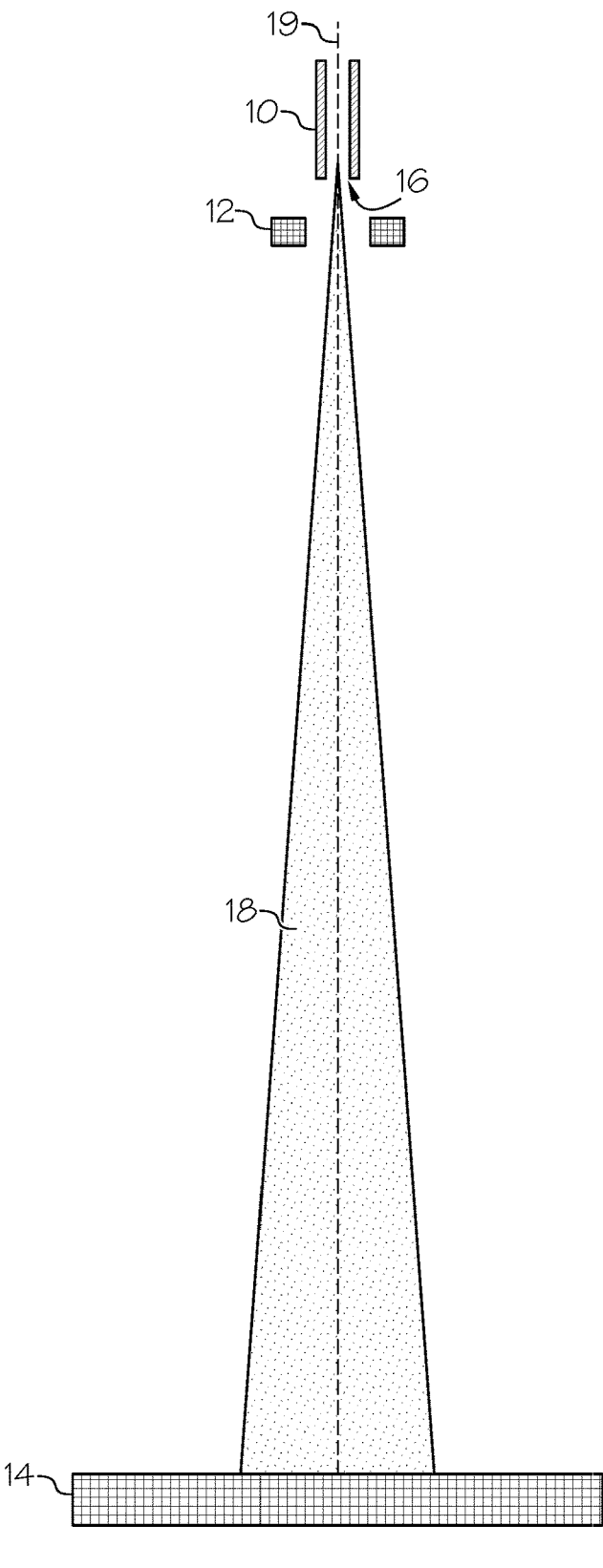
FIG. 1 is a schematic illustration of a known basic ESI configuration.

Reference in the specification to an embodiment or example means that a particular feature, structure or characteristic described in connection with the embodiment or example is included in at least one embodiment or example of the teaching. References to a particular embodiment or example within the specification do not necessarily all refer to the same embodiment or example.

As used herein, the term "nanospray" means a spray generated in an ESI process. By way of example, a nanospray may be produced from a solution where highly charged small droplets are formed by emission from a narrow-bore capillary or needle tip in the presence of a strong electric field (e.g., a few kV/cm). The term "nanospray plume" refers to the plume of droplets created in the ESI process. The term "nanodroplet" refers to a droplet within the nanospray plume. The size of the nanospray droplets within the plume generally decreasing with increasing distance from the capillary or emitter tip.

The term "electrosonic spray ionization (ESSI) is used herein to refer to an ionization technique that utilizes a high velocity nebulizing gas in conjunction with an ESI process to achieve a pneumatic spraying of the nanospray plume.

The term "counter electrode" is used herein to refer to an electrode having an aperture in which the end of the capillary, or needle tip, is disposed near or at the center of the aperture. Generally, the aperture has a circular shape.

The term "collection vessel" is used herein to refer to a vessel having a surface that is shaped to collect nanodroplets incident on the surface. For example, the collection vessel may be made from an electrically conductive material and have a concave surface on an upward facing side with respect to gravity. The concave surface allows liquid from incident nanodroplets to drip or flow toward the lowest position on the concave surface. The concave surface may be a conical surface or may have a curvature (i.e., a changing slope with respect to distance from the center of the surface). The collection vessel may have a channel that extends from the lowest position on the surface through the vessel to an outlet end. In a non-limiting example, a vacuum may be applied to the collection vessel to draw the liquid from the concave surface through the channel into a sample vial or other container to hold the collected liquid for analysis.

In brief overview, embodiments and examples disclosed herein are directed to an apparatus for generating and collecting nanospray reactive droplets and to methods for analyzing a protein digestion that can be performed using the apparatus. The apparatus includes components similar to those used to generate a nanospray, such as an electrospray used for ESI and ESSI ionization techniques. The apparatus includes a capillary having an inlet to receive a flow of a liquid and an outlet to dispense the flow of liquid. The mixture may include a protein and an enzyme. The apparatus further includes a counter electrode, an electrostatic lens system, a collection vessel and a voltage control module. The outlet of the capillary is disposed in the aperture of the counter electrode. The electrostatic lens system is disposed along a nanospray path that extends between the capillary outlet and the collection vessel and includes two or more electrostatic lenses that pass a nanospray plume containing the nanospray reactive droplets. The voltage control module is in electrical communication with the other components of the apparatus and enables independent control of the voltage of the capillary, counter electrode, electrostatic lenses and collection vessel.

The electrostatic lenses shape the nanospray plume and concentrate the plume onto a concave surface of the collection vessel. Concentration of the plume means the diameter of the plume at the concave surface is reduced with respect to a diameter of the upstream plume. Preferably, the nanospray plume is concentrated to a diameter at the concave surface that is large enough to substantially avoid or eliminate the recombination of droplets that may occur in regions of plume convergence near the collection vessel yet small enough to ensure that most or all the nanospray plume is incident on the concave surface.

The collection vessel may be perforated to permit the collection or extraction of the components of the nanospray plume on the concave surface. In some instances, the nanodroplets on the concave surface dry to leave a residue. In such instances, a solvent may be applied to the dried components on the concave surface to generate a resuspended sample that may be extracted from the collection vessel.

Advantageously, the apparatus enables a significant increase in the reaction rate due to the spatial confinement of the mixture in the nanospray droplets as compared to the reaction rate for a bulk mixture. Although electrostatic lenses are known for use in applications to direct a nanospray, such applications are limited to injecting the nanospray after exiting an analytical system (e.g., a liquid chromatography system) into a mass spectrometer for detection of analytes. Apparatus described herein enable the collection of samples (e.g., peptides) from the nanospray reactive droplets and provision of the sample to analytical equipment such as an LC-MS system.

The present teaching will now be described in detail with reference to exemplary embodiments or examples thereof as shown in the accompanying drawings. While the present teaching is described in conjunction with various embodiments and examples, it is not intended that the present teaching be limited to such embodiments and examples. On the contrary, the present teaching encompasses various alternatives, modifications, and equivalents, as will be appreciated by those of skill in the art. Those of ordinary skill having access to the teaching herein will recognize additional implementations, modifications, and embodiments, as well as other fields of use, which are within the scope of the present disclosure as described herein.

Many reactions and enzymatic digests LC-MS analysis require extensive reaction times. Thus, these preparative steps are often the rate-limiting factor in receiving LC-MS data for particular quality attributes in bioprocess applications. Microfluidic transport and nanodroplet formation are known to facilitate reaction acceleration due to dipole alignment and concentration effects along phase interfaces. These techniques have been demonstrated for small molecule reactions and protein-enzyme digestions using direct infusion into a mass spectrometer; however, infusion of heterogeneous mixtures results in ion suppression. As a result, failed identification of low abundance, modified peptides is possible. In addition, the buffers and reagents typically used for protein digests are often non-volatile and therefore are not ideal for direct mass spectrometry analysis. Application of ESI techniques to solutions results in the formation of a droplet plume in which nascent droplets formed at the tip of an emitter sequentially evaporate and collect charge before undergoing repeated fission events to generate smaller droplets. These techniques result in a diverging nanodroplet plume that rapidly expands in diameter and is difficult to directly collect. In addition, the tendency of the high-velocity droplets to bounce off a collection surface makes collection more difficult which can be especially problematic as droplet diameter decreases.

FIG. 1 is a schematic illustration of a basic ESI configuration as is known in the art. The components include a capillary 10, a counter electrode 12 and a target electrode 14. The voltage applied to the capillary 10 may be several thousand volts greater than the voltage (e.g., ground) of the target electrode 14. The counter electrode 12 may be at a voltage that is less than the capillary voltage by 2 kV volts or more. As a result of the electric field established by the voltages of the three components, the liquid carrying analytes of interest is dispensed from the capillary outlet 16 as a diverging aerosol plume 18 containing charged nanodroplets. The nanodroplets within the plume 18 are accelerated toward the target electrode 14 and generally include droplets of different sizes. Desolvation of the nanodroplets occurs with subsequent fission events to generate smaller sized nanodroplets as the distance from the capillary outlet 16 increases. This process continues as the formed nanodroplets accelerate toward the target electrode 14. Small solvated ions are ejected from the nanodroplets and deposited on the target electrode 14 and/or charged analytes are formed as the nanodroplets evaporate. In some instances, some or all the nanodroplets may not evaporate before arriving at the target electrode 14. The cross-section of the plume 18 increases with increasing distance from the capillary outlet 16 therefore the area on which the plume 18 is incident at the target electrode 14 may be large. In addition, the droplet size distribution within the plume 18 may vary significantly. For example, larger nanodroplets may be farther away from the spray axis 19 while smaller droplets tend to be closer to the spray axis 19.

Figure 2:
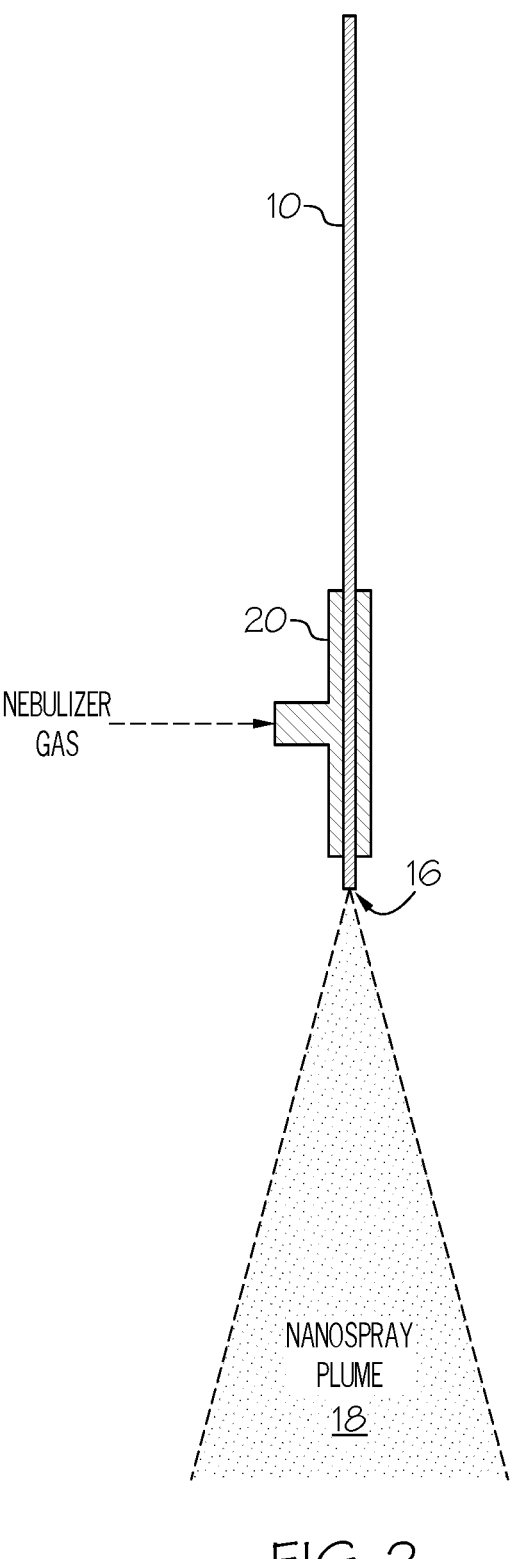
FIG. 2 depicts a known simplified electrospray configuration using a nebulizing gas.

In one simplified electrospray configuration shown in FIG. 2, a nebulizer 20 is arranged near the capillary outlet 16 to introduce a nebulizing gas, such as nitrogen or carbon dioxide, to the diverging aerosol plume 18 leaving the capillary 10. The result may be a plume 18 having reduced divergence; however, the cross-section of the plume 18 still generally increases as the droplets approach the target electrode. In some instances, the nebulizer 20 may have a pair of gas inlets to receive a nebulizing gas so that the gas dispensed from the nebulizer 20 is substantially balanced and concentric with the axis of the plume 18. Although not explicitly shown in the examples of an apparatus for generating and collecting nanospray reactive droplets described below, it will be recognized that the ESI processes used in those examples may be supplemented with a nebulizing gas.

Figure 3:
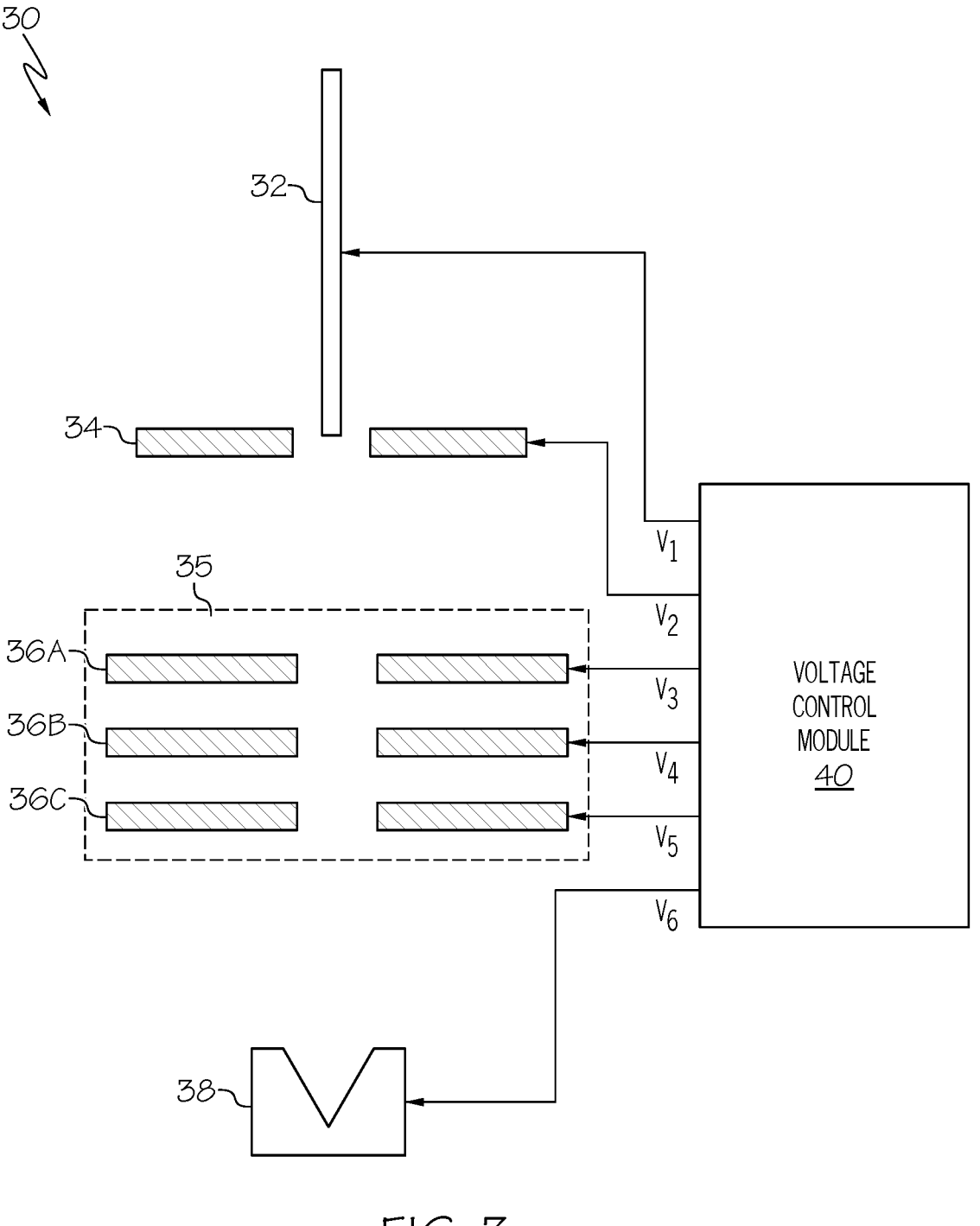
FIG. 3 is a schematic depiction of an example of an apparatus for generating and collecting nanospray reactive droplets.

FIG. 3 is a schematic depiction of an example of an apparatus 30 for generating and collecting nanospray reactive droplets. The apparatus 30 includes a capillary 32, a counter electrode 34, an electrostatic lens system 35, a collection vessel 38 and a voltage control module 40. The electrostatic lens system 35 is shown as having three electrostatic lenses 36A, 36B and 36C; however, in other examples the number of electrostatic lenses 36 may be only two or may be four or greater. The voltage control module 40 is in electrical communication with the capillary 32, counter electrode 34, each of the electrostatic lenses 36 and the collection vessel 38 either by wire, cables and/or other forms of electrically conductive paths. The voltage control module 40 enables independent control of the voltages ($V_1$, $V_2$, $V_3$, $V_4$, $V_5$ and $V_6$, as illustrated) of these components. In some implementations, one of the voltages (e.g., $V_6$) may be electrical ground.

Figure 4A:
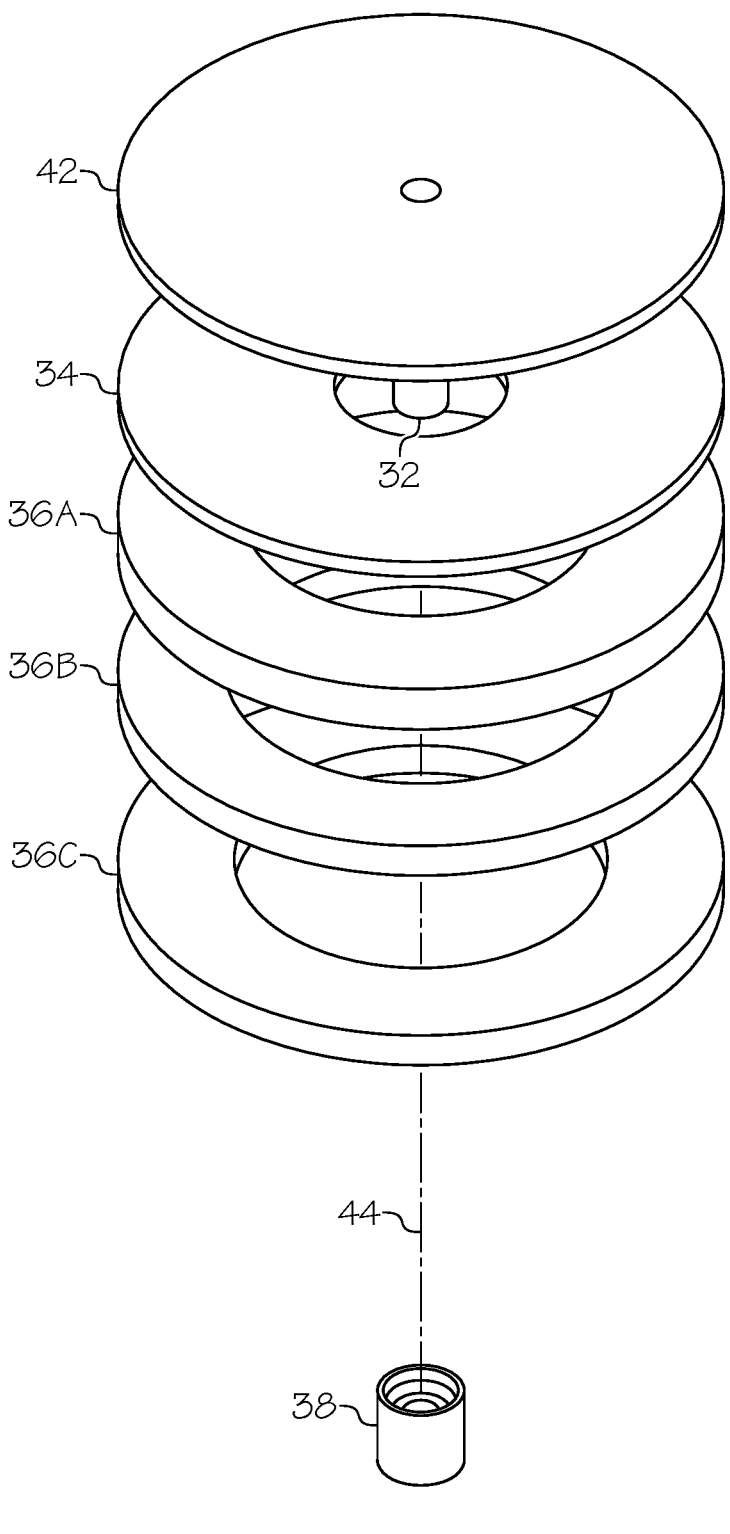
FIGS. 4A and 4B show a perspective illustration and a perspective cutaway illustration, respectively, of an example of the apparatus of FIG. 3 without the voltage control module.
Figure 4B:
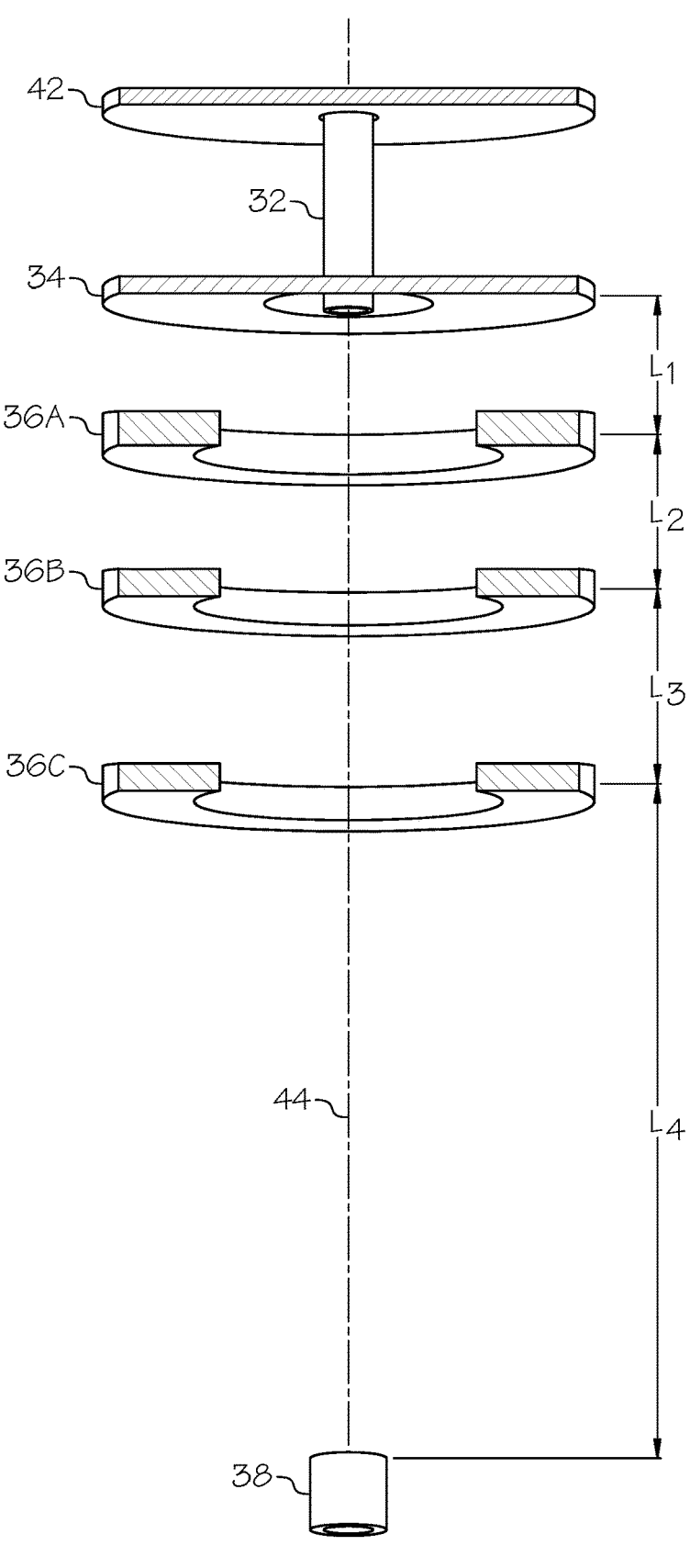

FIGS. 4A and 4B show a perspective illustration and a perspective cutaway illustration, respectively, of the apparatus 30 schematically illustrated in FIG. 3 with the voltage control module 40 excluded. In these illustrations, an additional plate 42 used for alignment with respect to the other components is shown. The alignment plate 42 is coupled to and concentric with the capillary 32. The components are arranged concentrically along a vertical nanospray path 44. The first lens 36A is spaced apart from the counter electrode 32 and capillary outlet 33 by a distance $L_1$. The first and second lenses 36A and 36B are spaced apart by a distance $L_2$ and the second and third lenses 36B and 36C are spaced apart by a distance $L_3$. The distance between the third lens 36C and the collection vessel 38 is a distance $L_4$.

The counter electrode 34 and electrostatic lenses 36 are formed as electrically conductive plates each having a circular aperture. Although illustrated as circular, the outer edge of the plates may have another shape such as a square. The capillary outlet 16 is disposed near or at the center of the aperture in the counter electrode 34. The plate thicknesses and aperture diameters may differ. By way of a non-limiting numerical example, plate thicknesses may be in a range of approximately 4 mm to 8 mm.

Figure 5:
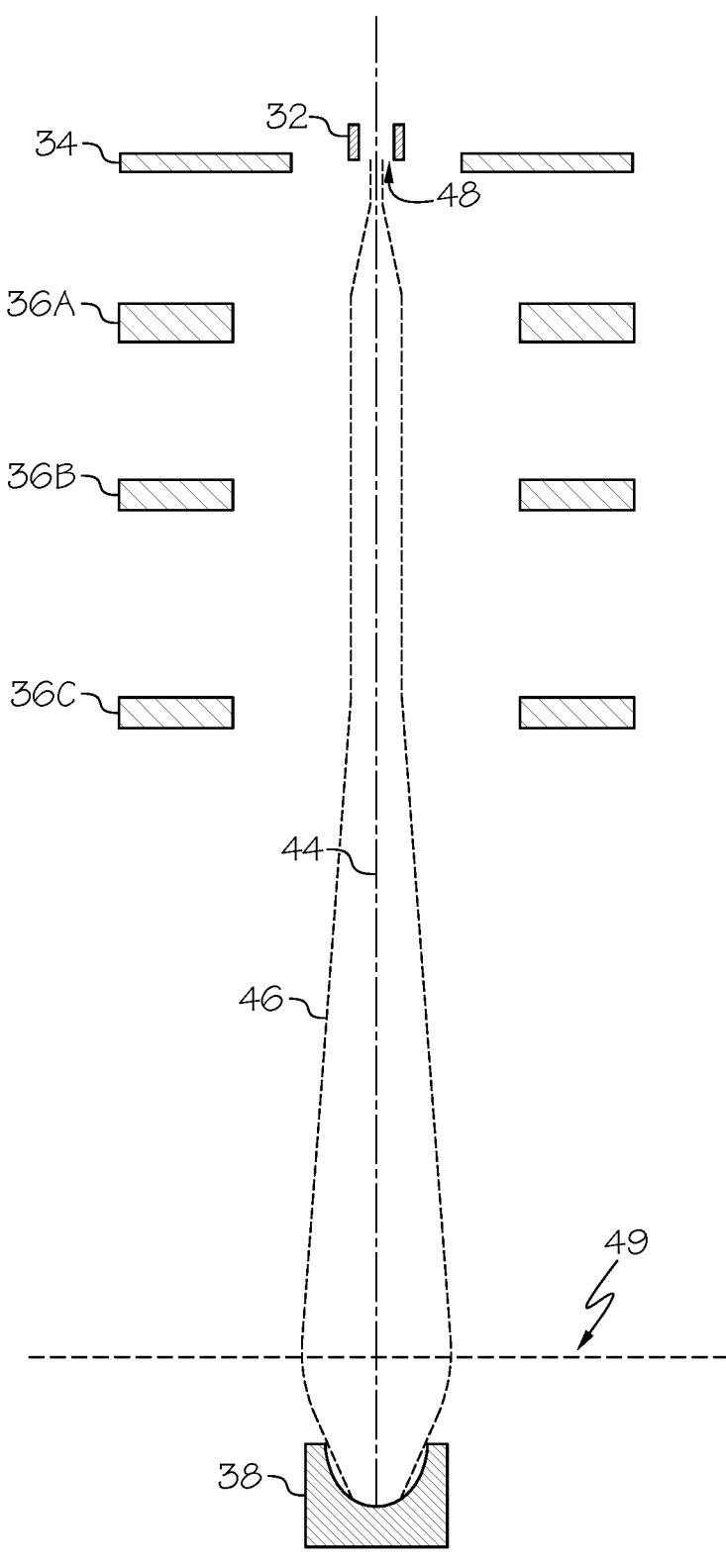
FIG. 5 is a cross-sectional depiction of the components in FIGS. 4A and 4B with a nanospray reactive plume.

The electric field generated within a volume defined between the counter electrode 34 and the collection vessel 38 and which includes the electrostatic lenses 36 is defined, in part, by the voltages $V_1$ to $V_6$, the dimensions of the counter electrode 34 and the electrostatic lenses 36, and the spacings $L_1$ to $L_4$ between the components. Adjustment of these parameters is used to control the shape of the nanospray plume. For example, FIG. 5 shows a cross-sectional depiction of the components in FIGS. 4A and 4B with a nanospray reactive plume 46 that diverges upon emission from the capillary outlet 48. By way of a non-limiting numerical example, the voltages are:

$V_1$=5-8.0 kV
$V_2$=2.5-4 kV
$V_3$=2.5-6 kV
$V_4$=1.8-2.7 kV
$V_5$=0.2-1.8, customarily 1.5 kV
$V_6$=0 V (ground)

the aperture diameter of the counter electrode is approximately 22 mm and the electrostatic lens aperture diameters are approximately 40 mm, and the separations are:

$L_1$=10-12 mm
$L_2$=20-30 mm
$L_3$=20-50 mm
$L_4$=70-140 mm

Preferably, the aperture dimensions and operating parameters (voltages V and component separations L) are selected to maximize the collection of the nanodroplets at the collection vessel 38. For example, the dimensions and operating parameters may be determined according to the composition of the mixture provided to the capillary 32. The surface diameter and surface slope (or surface curvature) of the collection vessel 38 may affect the preferred dimensions and operating parameters. Likewise, it should be recognized that the physical properties of the nanodroplets affects the preferred dimensions and operating parameters. For example, if additional buffer and protein are included in the nanodroplets, the nanodroplets become more viscous and their surface tension is increased. Consequently, a higher electric field strength may be necessary for the liquid to be formed into a nanospray, especially as defined by the voltage difference between the capillary 32 and the counter electrode 34.

In the illustrated example, the plume 46 no longer expands as the nanodroplets pass through the aperture of the first electrostatic lens 36A and there is a small plume convergence (i.e., reduction in plume diameter) as the nanodroplets approach and pass through the aperture of the second electrostatic lens 36B. The plume diameter remains nearly constant until the plume 46 exits from the aperture of the third electrostatic lens 36C where the plume 46 expands until reaching a maximum plume diameter (at dashed line 49) before converging until the plume 46 is incident at the collection vessel 38.

Experimental Demonstration

Figure 6:
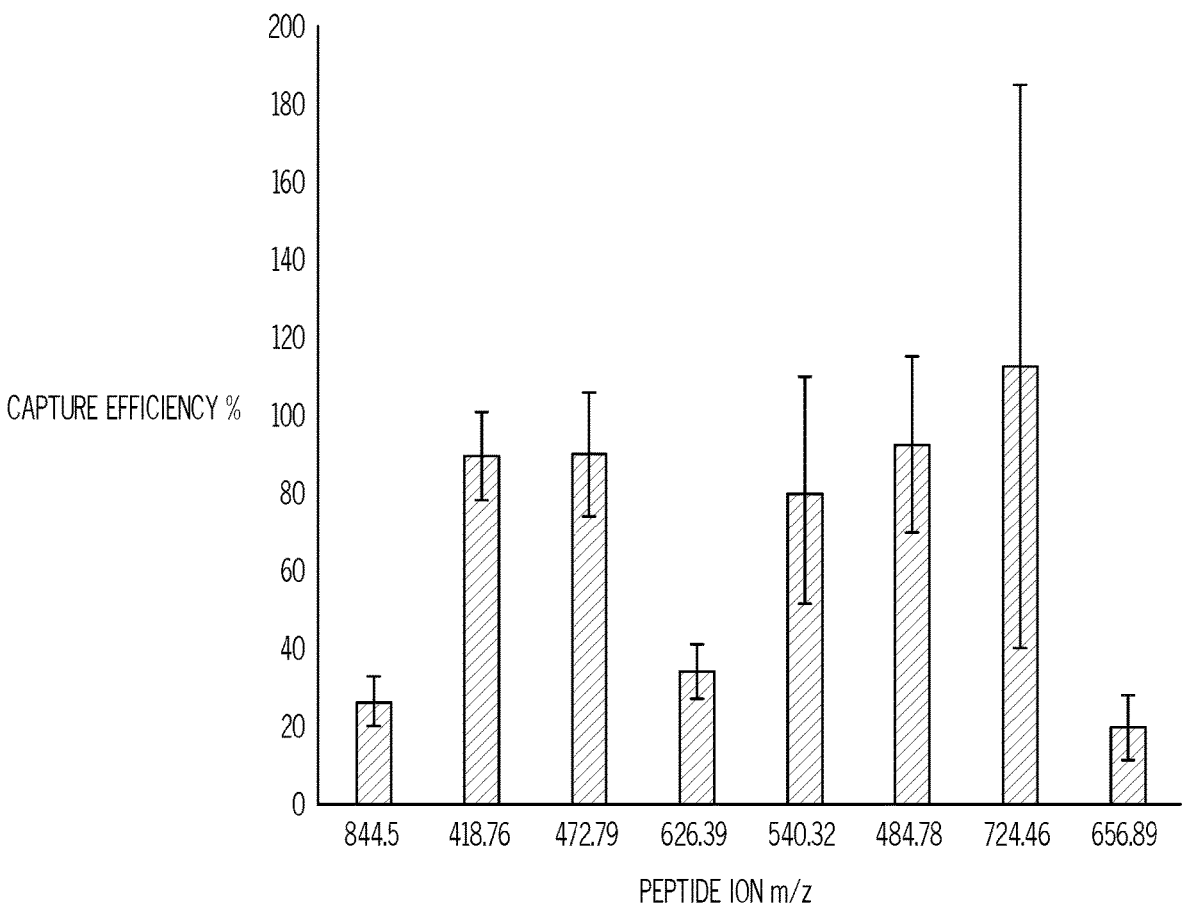
FIG. 6 is a graphical representation of the nanodroplet collection efficiency for the apparatus of FIGS. 4A and 4B for eight different predigested peptide digests of alcohol dehydrogenase.

An experimental demonstration of nanodroplet collection efficiency was performed using a predigested peptide digest of alcohol dehydrogenase. Eight peptides were examined and the results are shown in FIG. 6. Five of the evaluated peptides were collected with greater than 80% efficiency. The remaining three peptides were collected at lower efficiencies of approximately 20%. Each of those three peptides has a N-terminal serine residue, which may impact the ionization mechanisms for the peptide.

Figure 7:
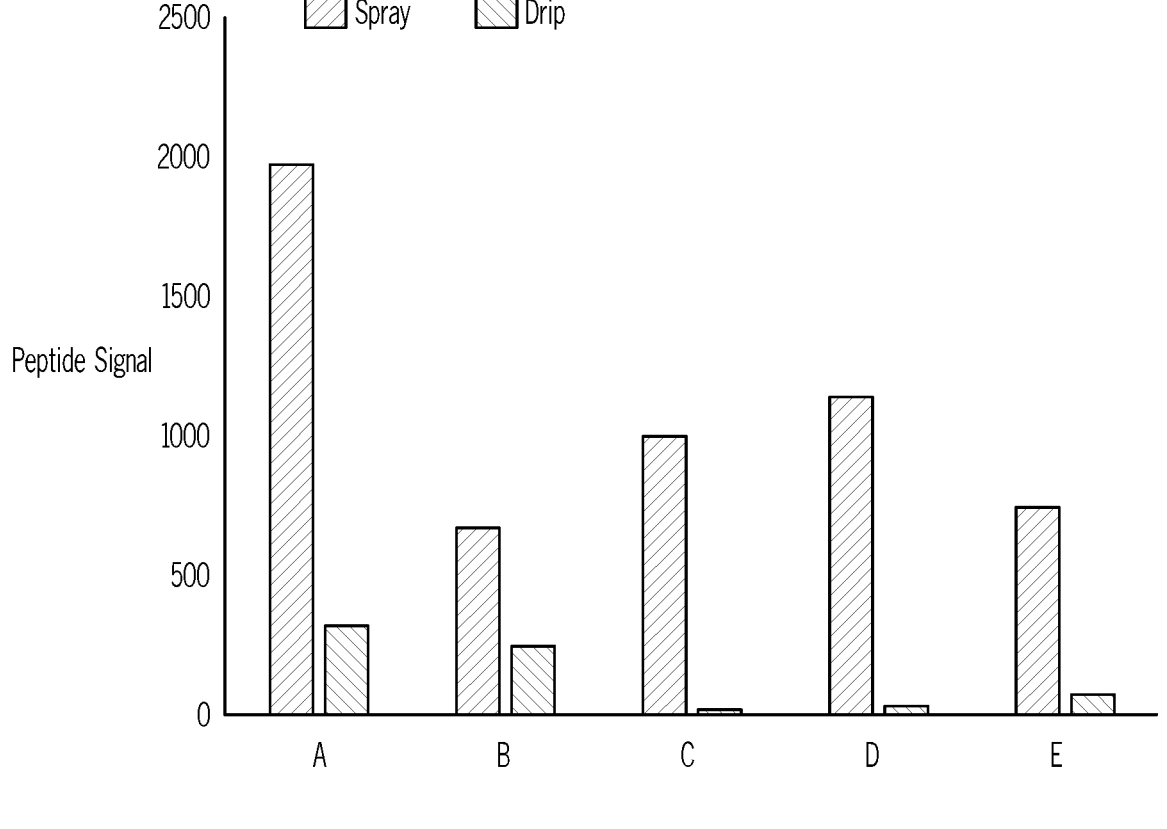
FIG. 7 is a graphical representation of the relative abundance of five tryptic peptides measured using the apparatus of FIGS. 4A and 4B for both electrospray and control mode operation.

In another demonstration, five tryptic peptides from an electrospray digest of a monoclonal antibody were measured using an apparatus configured as described above at a flow rate of 5 μL/min. Two collections were performed in which the proteins were mixed via an infusion apparatus; however, one of the collections was a control ("Drip") collection in which electrospraying was omitted and the liquid was collected from the electrospray emitter. For each collection, protein material was collected for five minutes and rehydrated and quenched with 6M guanidine hydrochloride prior to performing an LC-MS analysis. The relative abundance of the digested peptides is shown in FIG. 7.

Another evaluation of the apparatus for generating and collecting nanospray reactive droplets, as described for the apparatus examples above, was performed. A protein (a monoclonal antibody) was mixed in bulk with buffers for stabilization and a peptide standard was added to address collection efficiency defined as the amount of sample retrieved from the collection vessel. A first assessment addressed what happens in bulk solutions maintained in a test vial after mixing. Second, a control mode operation of the apparatus in which the liquid exiting at the capillary outlet was allowed to drip into the collection vessel (i.e., no electrospray process was used) was examined. A third assessment was based on operation of the apparatus using a pneumatically assisted ESI process where a substantially balanced laminar nebulization gas flow was introduced adjacent to the capillary outlet. The flow rate through the capillary for the control mode operation and pneumatically assisted ESI operation was 5 μL/min. Some low reaction rate occurs for the bulk solution during the five minutes while some reaction rate acceleration occurs while the mixture traverses the microfluidics to the capillary outlet over approximately 12 seconds. The reaction rate accelerates significantly during the 70 ms time when the nanodroplets propagate from the capillary outlet to the collection vessel. For this reason, it may be desirable in alternative configurations to increase the distance between the capillary outlet and the collection vessel to increase nanodroplet lifetimes and thereby increase the time for reaction in the nanospray plume.

Figure 8:
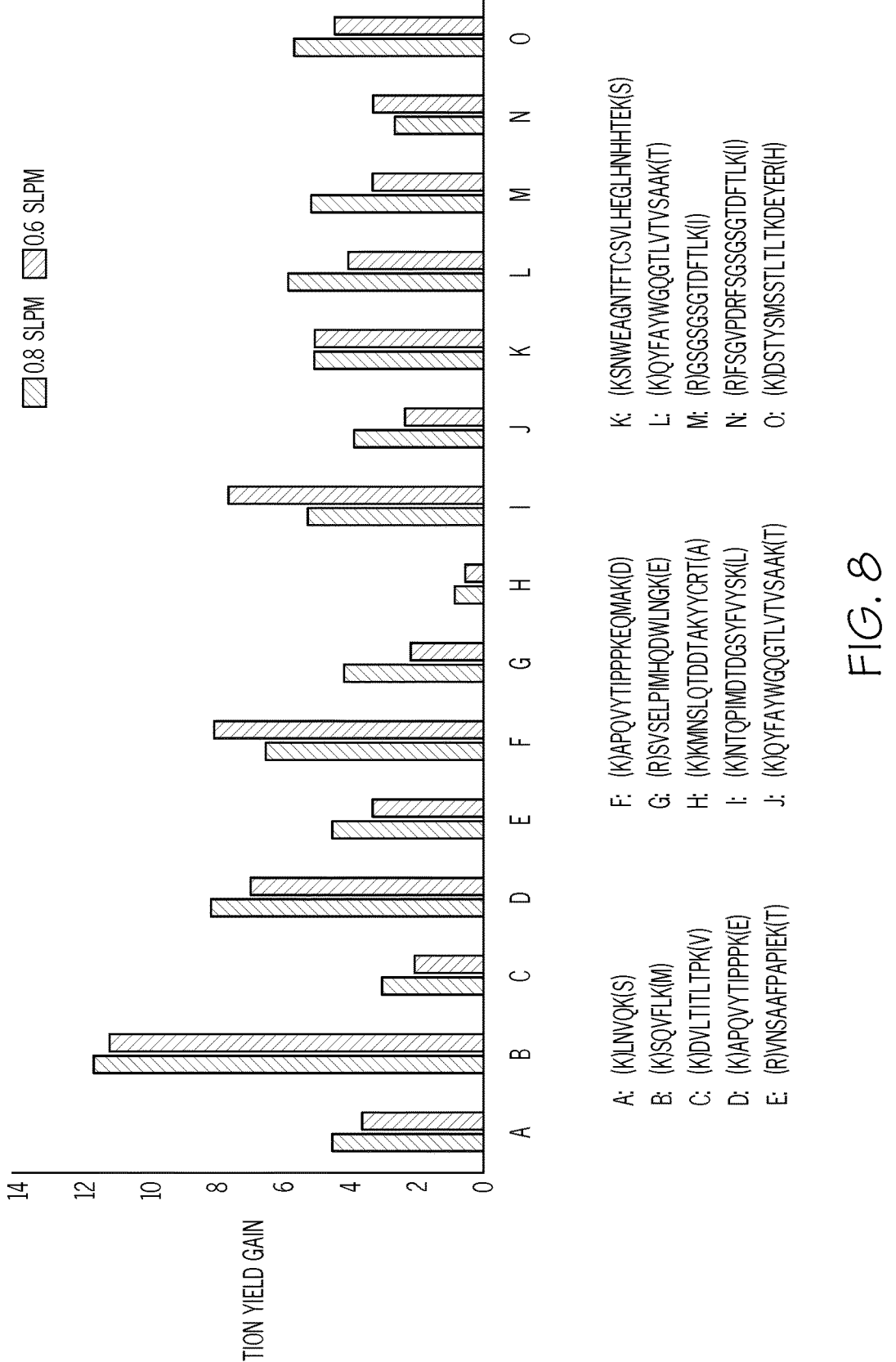
FIG. 8 is a graphical representation of collection yield gain for different monoclonal antibody samples for the apparatus of FIGS. 4A and 4B using two different nebulizer gas flow rates.

At the end of the five minute collection period, the collected samples were quenched with protein to eliminate the enzymes and effectively stop further reactions. FIG. 8 shows the determined collection yield gain for different samples where each sample was measured using a nebulizing gas flow of 0.6 standard liters/min (SLPM) and 0.8 SLPM gas flow. The collection yield efficiency is defined as the average peptide signal, corrected for capture efficiency, divided by the average peptide signal determined under control mode operation. This corrected average signal is the signal of each replicate divided by the collection efficiency of the replicate. The collection efficiency is the signal of an internal standard (i.e., the average of the observed peptides) in the collected replicate divided by the average internal standard signal from control mode operation. A yield gain of one corresponds to an identical collection for the control configuration and the pneumatically assisted electrospray configuration.

While various examples have been shown and described, the description is intended to be exemplary, rather than limiting and it should be understood by those of ordinary skill in the art that various changes in form and detail may be made therein without departing from the scope of the invention as recited in the accompanying claims.

What is claimed is:

1. An apparatus for generating and collecting nanospray reactive droplets comprising:
 a capillary having a capillary inlet that receives a mixture of a protein and an enzyme and a capillary outlet to dispense the mixture;
 a counter electrode formed of an electrically conductive plate having an aperture therein wherein the capillary outlet is disposed in the aperture;
 a collection vessel formed of an electrically conductive material and having a concave surface configured to receive a nanospray plume emitted from the capillary outlet, wherein the capillary and the collection vessel are disposed on a nanospray path extending between the capillary outlet and the collection vessel;
 a plurality of electrostatic lenses disposed along the nanospray path, each electrostatic lens formed of an electrically conductive plate having an aperture therein, said aperture configured to pass the nanospray plume; and a voltage control module in electrical communication with and configured to independently control the voltage of the capillary, the counter electrode, the collection vessel and each of the electrostatic lenses.

2. The apparatus of claim 1 wherein the concave surface is a conical surface.

3. The apparatus of claim 1 wherein the collection vessel is perforated to enable liquid comprising nanospray reactive droplets incident on the concave surface to be extracted.

4. The apparatus of claim 1 further comprising a nebulizer disposed proximate to the capillary outlet and having a mixture inlet to receive the mixture of the protein and the enzyme, a gas inlet to receive a nebulizer gas and a nebulizer outlet to provide a nebulized flow of the dispensed mixture.

5. The apparatus of claim 4 wherein the gas inlet includes a pair of gas inlets wherein the gas inlets are disposed diametrically opposite to each other with respect to an axis defined between the mixture inlet and the nebulizer outlet.

6. The apparatus of claim 1 wherein a position of each of the electrostatic lenses along the nanospray path is adjustable.

7. The apparatus of claim 1 wherein the nanospray path is oriented vertical with respect to gravity.

8. A method for analyzing a protein digestion, the method comprising:

providing a solution containing a protein and an enzyme;

electrospraying the solution to form a nanospray plume of nanodroplets to accelerate a protein digestion; and concentrating the nanospray plume onto a surface of a collection vessel formed of an electrically conductive material and having a concave surface to receive the nanospray plume emitted from a capillary outlet;

wherein the nanospray plume passes through an aperture of one of one of a plurality of electrostatic lenses disposed along a nanospray path, each electrostatic lens formed an electrically conductive plate having an aperture therein; and wherein a voltage of the capillary outlet, a counter electrode, the collection vessel and each of the electrostatic lenses is independently controlled via a voltage control module.

9. The method of claim 8 wherein a diameter of the nanospray plume at the collection vessel is less than a maximum diameter of the nanospray plume at an upstream position in the nanospray path.

10. The method of claim 8 further comprising collecting a liquid formed by the nanospray plume incident at the surface of the collection vessel to generate a sample.

11. The method of claim 10 wherein collecting the liquid comprises drying the liquid on the surface of the collection vessel to generate a residue and subsequently solvating the residue to generate a resuspended sample.

12. The method of claim 10 further comprising performing a liquid chromatography analysis of the sample.

13. The method of claim 11 further comprising performing a liquid chromatography analysis of the resuspended sample.

14. The method of claim 12 wherein providing the solution comprises providing a solution containing a protein, an enzyme and one or more buffer components.

\* \* \* \* \*